(12) United States Patent
Chen et al.

(10) Patent No.: US 8,000,905 B1
(45) Date of Patent: Aug. 16, 2011

(54) COMPUTER-IMPLEMENTED METHODS, CARRIER MEDIA, AND SYSTEMS FOR DETERMINING SIZES OF DEFECTS DETECTED ON A WAFER

(75) Inventors: Stephanie Chen, Fremont, CA (US); Subramanian Balakrishnan, Cupertino, CA (US); Richard Wallingford, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 593 days.

(21) Appl. No.: 11/855,589

(22) Filed: Sep. 14, 2007

(51) Int. Cl.
*G01B 5/28* (2006.01)
(52) U.S. Cl. ......................................................... 702/35
(58) Field of Classification Search .................... 702/35, 702/36, 85, 166, 179, 182, 183
See application file for complete search history.

(56) References Cited

U.S. PATENT DOCUMENTS 7,474,394 B2 * 1/2009 Hamamatsu et al. ...... 356/237.2
7,599,051 B1 * 10/2009 Labovitz et al. ........... 356/237.2

OTHER PUBLICATIONS

Stokowski et al. "Wafer Inspection Technology Challenges for ULSI Manufacturing," AIP Conf. Proc., vol. 449, Nov. 24, 1998, pp. 405-415.

* cited by examiner

*Primary Examiner* — Drew A Dunn
*Assistant Examiner* — Stephen J Cherry
(74) *Attorney, Agent, or Firm* — Ann Marie Mewherter

(57) ABSTRACT

Computer-implemented methods, carrier media, and systems for determining sizes of defects detected on a wafer are provided. One computer-implemented method includes separating the defects into groups based on output acquired for the defects by multiple channels of an inspection system used to detect the defects on the wafer. The method also includes separating the defects in one or more of the groups into subgroups based on the output acquired for the defects by one or more of the multiple channels. In addition, the method includes determining the sizes of one or more of the defects in one or more of the subgroups separately based on the output acquired for the defects by only one of the multiple channels and a calibration parameter. The calibration parameter is different for each of the subgroups and is acquired by using another system to measure actual sizes of defects detected on other wafers.

22 Claims, 3 Drawing Sheets

COMPUTER-IMPLEMENTED METHODS, CARRIER MEDIA, AND SYSTEMS FOR DETERMINING SIZES OF DEFECTS DETECTED ON A WAFER

BACKGROUND OF THE INVENTION

1. Field of the Invention

This invention generally relates to computer-implemented methods, carrier media, to and systems for determining sizes of defects detected on a wafer. Certain embodiments relate to a computer-implemented method for separating the defects into groups by defect type, separating the defects into subgroups by size, aspect ratio, gradient, or some combination thereof, and determining the sizes of the defects in different subgroups separately.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an import part of fabricating semiconductor devices such as integrated circuits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Many different types of inspection tools have been developed for the inspection of semiconductor wafers. Defect inspection is currently being performed using techniques such as bright field (BF) imaging, dark field (DF) imaging, and scattering. The type of inspection tool that is used for inspecting semiconductor wafers may be selected based on, for example, characteristics of the defects of interest and characteristics of the wafers that will be inspected. For example, some inspection tools are designed to inspect unpatterned semiconductor wafers or patterned semiconductor wafers.

Inspection tools for unpatterned wafers are generally not capable of inspecting patterned wafers for a number of reasons. For example, many unpatterned wafer inspection tools are configured such that all of the light collected by a lens or another collector is directed to a single detector that generates a single output signal representative of all of the collected light. Therefore, light scattered from patterns or other features on the specimen will be combined with other scattered light. As such, light scattered from patterns or other features on the wafer cannot be separated from other scattered light thereby hindering, if not preventing, defect detection.

Patterned wafer inspection is of particular interest and importance to the semiconductor industry because processed semiconductor wafers usually have a pattern of features formed thereon. Although inspection of unpatterned wafers, or "monitor wafers," which have been run through a process tool, may be used as a gauge for the number and types of defects that may be found on patterned wafers, or "product wafers," defects detected on monitor wafers do not always accurately reflect the defects that are detected on patterned wafers after the same process in the same process tool. Inspection of patterned wafers is, therefore, important to accurately detect defects that may have been formed on the wafer during, or as a result of processing. Therefore, inspecting patterned wafers or product wafers may provide more accurate monitoring and control of processes and process tools than inspection of monitor wafers.

Semiconductor processes can also be better controlled when more information and more accurate information about the defects detected on wafers is available for monitoring and controlling the processes. Therefore, it is desirable and advantageous to determine information about the defects such as size and to determine such information accurately. In general, two methods have been previously used for reporting defect size from dark field inspection systems. One method includes using defect pixel count to report defect size. Another method includes using scattering intensity from one channel of the dark field inspection system to report defect size.

There are, however, a number of disadvantages to these previously used methods for determining defect size. For instance, using defect pixel count reported by a scanning inspection system as the size can be substantially inaccurate and misleading. In addition, each pixel in the scanning inspection system can be as large as several microns. Therefore, the error in the defect size can be on the order of several microns. Dark field scanning systems do not resolve the defect shape since the point spread function (PSF) is typically several pixels in extent.

In another instance, using scattering intensity to report defect size is more accurate than using pixel count since the scattering intensity is typically some function of defect size. However, there are several factors making the size reporting inaccurate using scattering intensity only. For example, defect shape and cross section profile can affect the scattering intensity. In addition, materials may also affect the scattering intensity. Moreover, the surface roughness may affect scattering intensity. Therefore, the performance of this method is usually only good on particles and is poor for other defect types such as flat, planar, and void types of defects.

Accordingly, it would be advantageous to develop computer-implemented methods, carrier media, and/or systems for determining sizes of defects detected on wafers more accurately than previously used methods and more accurately for different types of defects than previously used methods.

SUMMARY OF THE INVENTION

The following description of various embodiments of computer-implemented methods, carrier media, and systems is not to be construed in any way as limiting the subject matter of the appended claims.

One embodiment relates to a computer-implemented method for determining sizes of defects detected on a wafer. The method includes separating the defects into groups based on output acquired for the defects by multiple channels of an inspection system used to detect the defects on the wafer. The method also includes separating the defects in one or more of the groups into subgroups based on the output acquired for the defects by one or more of the multiple channels. In addition, the method includes determining the sizes of the defects in one or more of the subgroups separately based on the output acquired for the defects by only one of the multiple channels and a calibration parameter. The calibration parameter is different for each of the subgroups. In addition, the calibration parameter is acquired by using another system to measure actual sizes of defects detected on other wafers.

In one embodiment, the inspection system includes a dark field inspection system. In another embodiment, the method includes determining a distribution of the sizes of at least some of the defects detected on the wafer and monitoring a process performed on the wafer based on the distribution.

In one embodiment, the output acquired by the multiple channels used to separate the defects into the groups includes scattering intensity. In another embodiment, the groups are defined based on how different types of defects scatter light into the multiple channels. In an additional embodiment, the groups are defined such that different groups correspond to different types of defects.

In one embodiment, the output acquired by the one or more of the multiple channels used to separate the defects into the subgroups includes one or more properties of images of the defects. In one such embodiment, the one or more properties include a scattering intensity, an area, a gradient, or some combination thereof. In another embodiment, the subgroups are defined based on a correlation between the output acquired by the one or more of the multiple channels for the defects detected on the other wafers and the actual sizes of the defects detected on the other wafers. In an additional embodiment, the subgroups are defined such that different subgroups correspond to different size ranges of the defects. In a further embodiment, the subgroups are defined such that different subgroups correspond to different size ranges of the defects, different heights of the defects, and different layers on which the defects were detected. In some embodiments, separating the defects into subgroups includes determining scattering intensity and area of the defects using the output acquired by the one or more of the multiple channels and the scattering intensity from the defects.

In one embodiment, the output acquired by the only one of the multiple channels used to determine the sizes of the one or more of the defects includes scattering intensity and area of the defects. In another embodiment, the output acquired by the only one of the multiple channels used to determine the sizes of the one or more of the defects includes total scattering energy from the defects. In some embodiments, the only one of the multiple channels includes a normalized channel.

In one embodiment, the determining step includes determining the sizes of the one or more of the defects in the one or more of the subgroups separately using different types of functions for at least two of the subgroups. In one such embodiment, the different types of functions are based on the output acquired for the defects by the only one of the multiple channels and the calibration parameters. In another embodiment, the determining step includes determining the sizes of the one or more of the defects in the one or more of the subgroups separately using the same type of function for at least two of the subgroups. In one such embodiment, the same type of function for each of the at least two of the subgroups is based on the calibration parameter that is different for each of the subgroups.

In one embodiment, the defects are detected on different layers on the wafer. In one such embodiment, the sizes determined for the defects detected on the different layers that are separated into the same subgroup are determined using different calibration parameters. In another such embodiment, the sizes determined for the defects detected on the different layers that are separated into the same subgroup are determined using the same calibration parameter.

Each of the steps of the method described above may be performed as described further herein. In addition, each of the embodiments of the method described above may include any other step(s) of any other method(s) described herein. Furthermore, each of the embodiments of the method described above may be performed by any of the systems described herein.

Another embodiment relates to a carrier medium that includes program instructions executable on a computer system for performing a computer-implemented method for determining sizes of defects detected on a wafer. The computer-implemented method includes separating the defects into groups based on output acquired for the defects by multiple channels of an inspection system used to detect the defects on the wafer. The method also includes separating the defects in one or more of the groups into subgroups based on the output acquired for the defects by one or more of the multiple channels. In addition, the method includes determining the sizes of one or more of the defects in one or more of the subgroups separately based on the output acquired for the defects by only one of the multiple channels and a calibration parameter. The calibration parameter is different for each of the subgroups. The calibration parameter is acquired by using another system to measure actual sizes of defects detected on other wafers.

The carrier medium described above may be further configured as described herein. The steps of the computer-implemented method may be performed as described further herein. In addition, the computer-implemented method for which the program instructions are executable may include any other step(s) of any other method(s) described herein.

An additional embodiment relates to a system configured to determine sizes of defects detected on a wafer. The system includes an inspection system configured to detect the defects on the wafer and to acquire output for the defects. The system also includes a computer system configured to separate the defects into groups based on the output acquired for the defects by multiple channels of the inspection system. The computer system is also configured to separate the defects in one or more of the groups into subgroups based on the output acquired for the defects by one or more of the multiple channels. In addition, the computer system is configured to determine the sizes of one or more of the defects in one or more of the subgroups separately based on the output acquired for the defects by only one of the multiple channels and a calibration parameter. The calibration parameter is different for each of the subgroups. The calibration parameter is acquired by using another system to measure actual sizes of defects detected on other wafers. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
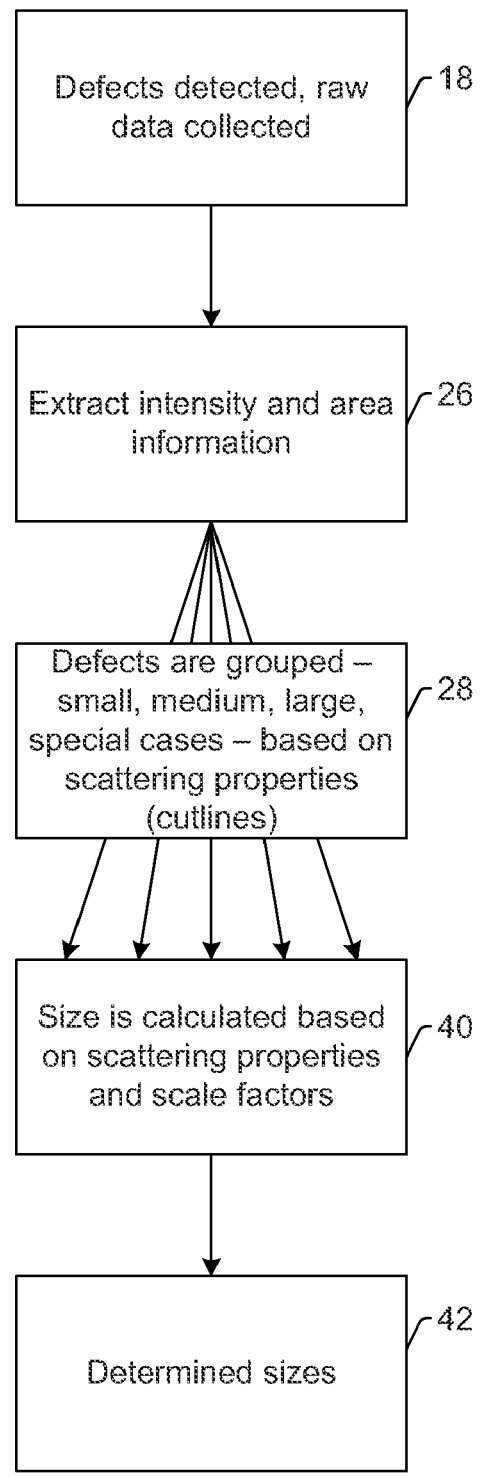
FIG. 1 is a flow chart illustrating one embodiment of a computer-implemented method for determining sizes of defects detected on a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although various embodiments are described herein with respect to defects detected on wafers, it is to be understood that all of the embodiments described herein can be used for determining the sizes of defects detected on any other suitable specimen such as a reticle. The terms "reticle," "mask," and "photomask" are used interchangeably herein. A reticle generally includes a transparent substrate such as glass, borosilicate glass, and fused silica having patterned regions of opaque material formed thereon. The opaque regions may be replaced by regions etched into the transparent substrate. Many different types of reticles are known in the art, and the term reticle as used herein is intended to encompass all types of reticles.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Laser scattering defect inspection systems provide a wealth of information about defect size and defect distribution at substantially high throughput. However, as described further herein, such optical systems provide limited accuracy for defect sizes through detected pixels or intensity because of the fundamentally limited nature of this technique. For example, the scattering intensity detected by dark field inspection systems depends on defect size, shape, surface roughness, material, etc. of an inspected object. Therefore, defect size is related to scattering intensity. The challenge is how to report a defect size accurately based on the information collected from the dark field inspection system such as scattering intensity and number of anomalous pixels (NAP) from a defect.

There is, therefore, a desire to provide improved defect size reporting accuracy in scattering inspection systems. In addition, with more accurate defect size reporting in real time, defect size distribution of wafers can be monitored to control semiconductor processes. The embodiments described herein generally relate to determining defect sizes with improved accuracy over currently used methods. In general, the embodiments described herein utilize defect scattering intensity and area information from single or multiple channels (collectors) of an inspection system with "ground-truth" data to improve the accuracy of the determination of the defect size.

One embodiment relates to a computer-implemented method for determining sizes of defects detected on a wafer. FIG. 1 illustrates one embodiment of such a computer-implemented method. It is noted that the steps shown in FIG. 1 are not essential to practice of the method. One or more steps may be omitted or added to the method illustrated in FIG. 1, and the method can still be practiced within the scope of these embodiments.

In some embodiments, as shown in FIG. 1, the method includes detecting defects and collecting raw data as shown in step 18 of FIG. 1. The defects may be detected and the raw data for the defects may be collected using an inspection system as described further herein. For example, in one embodiment, the inspection system includes a dark field inspection system. In this manner, the embodiments described herein can be used to determine defect size on dark field inspection systems. In some embodiments, the dark field inspection system may be configured for inspection of patterned wafers; however, such an inspection system may also be used for inspection of unpatterned wafers. In addition, the inspection system may be configured to collect and detect light scattered from the defects using multiple channels, which may be configured as described further herein.

The defects that are detected may include any of the defects described herein and any other defects of interest, which may vary depending on the wafer being inspected and/or the process performed on the wafer prior to inspection. The raw data that is collected may include any suitable raw data that can be used in the methods described herein. For example, the raw data may include image data. In addition, the raw data that is collected in this step may vary depending on the inspection system used to inspect the wafer. Furthermore, the raw data may include any of the output described further herein.

Detecting defects and collecting the raw data may, therefore, include using an inspection system (e.g., a dark field inspection system) to inspect a wafer. However, the computer-implemented method does not necessarily include inspecting the wafer. For example, the computer-implemented methods described herein may include acquiring the output described further herein from an inspection system used to inspect the wafer. In one such example, the computer-implemented methods described herein may acquire the output by receiving the output from a processor of the inspection system or retrieving the output from a storage medium (e.g., a storage medium included in the inspection system, a fab database, etc.) in which the inspection system stored the output of the inspection process. The output may have any suitable format known in the art (e.g., a KLARF file or any other standard file format).

The embodiments described herein categorize defects into different groups and subgroups based on their scattering intensity and defect area from single or multiple channels. In particular, as described further herein, defect sizing is defined as a function, F, of intensity, area, and defect features. The intensity may be the intensity of the light scattered from the defects in images of the defects. The area may be the area of the light scattered from the defects in images of the defects. The defect features may be any other property of the defects that can be determined from images of the light scattered from the defects. The parameter set for the function, F, is bins (i.e., subgroups), cutlines (i.e., divisions between the bins, thresholds separating the bins, etc.), and calibration parameters. The bins may be defined based on the defect features, while the cutlines and calibration parameters may be defined based on "ground-truth" and measured data. For example, for some inspection systems, the bins may be defined for defect features such as different heights of the defects (e.g., relatively tall defects or relatively planar defects) and different layers on which the defects were detected (e.g., defects that appear relatively dim in images of light scattered from the defects). For other inspection systems, the bins may be defined differently.

The method includes separating the defects into groups based on output acquired for the defects by multiple channels of an inspection system used to detect the defects on the wafer. In one embodiment, the output acquired by the multiple channels used to separate the defects into the groups includes scattering intensity. For example, different defect types scatter light differently into different channels of an inspection system. Therefore, different defect types can be grouped accordingly. The output of the multiple channels used to separate the defects into groups may include the output generated by all of the channels of the inspection system. However, the output of the multiple channels used to separate the defects into groups may include the output generated by fewer than all of the channels of the inspection system.

In one such example, since the scattering properties of particle type defects, flat type defects, and void type defects detected by multiple channels are significantly different, the scattering properties of these defect types can be used to group the defects by type accordingly. Particles scatter light primarily toward the polar angle range from about 20 degrees to about 70 degrees. Void type defects scatter light primarily toward the normal collection channel (See, for example, "Wafer Inspection Technology Challenges for ULSI Manufacturing," Stokowski et al., which is incorporated by reference as if fully set forth herein). Using side collection channel and normal collection channel scattering information, therefore, defects may be separated into three different groups (or categories): particle, flat, and void.

Dark field inspection systems only collect the scattering intensity from the inspected object. The scattering intensity depends on defect size, shape, surface roughness, material, etc. of an inspected object. In this way, the method takes into account the shapes, materials, and surface roughness of defects and is more robust than other methods for determining defect sizes. For example, as will be described further herein, grouping the defects according to their types using multiple channel information avoids the error in determining defect size based on scattering images caused when defects of similar size scatter light differently thereby producing different scattering images and different defect sizes. In this manner, in some embodiments, the groups are defined based on how different types of defects scatter light into the multiple channels. In an additional embodiment, the groups are defined such that different groups correspond to different types of defects.

In some embodiments, the method includes extracting intensity and area information for the defects detected on the wafer, as shown in step 26 of FIG. 1. For example, in one embodiment, separating the defects into subgroups as described further herein includes determining scattering intensity and area of the defects using the output acquired by one or more of the multiple channels and the scattering intensity from the defects. For example, the method may include extracting n pixels by n pixels (for example, 32 pixels by 32 pixels) image patches from a detected channel around the defect locations reported by a detection algorithm used to detect the defects. Then, the method may include forming a more accurate defect blob within the image patch using any suitable algorithm.

From the defect blob, the mean intensity and the peak difference intensity (i.e., the peak intensity of the difference image for the defect) may be determined. The number of pixels that form the blob may also be reported.

The method also includes separating the defects in one or more of the groups into subgroups based on the output acquired for the defects by one or more of the multiple channels. For example, in this step, defects are separated into different subgroups by outlines based on the defect features. In one embodiment, the output acquired by the one or more of the multiple channels used to separate the defects into the subgroups includes one or more properties of images of the defects. The images are images of light scattered from the defects. In one such embodiment, the one or more properties include a scattering intensity, an area, a gradient, or some combination thereof. For example, the method may categorize defects into different subgroups based on their scattering intensity and defective area determined from output generated by a single channel of the inspection system or multiple channels of the inspection system.

The scattering intensity of the image of the defect may be determined in any suitable manner. The area of the image of the defect may be determined in any suitable manner such as by how many pixels are included in the area of the image of the defect. The gradient may be determined in any suitable manner.

In another embodiment, the subgroups are defined based on a correlation between the output acquired by the one or more of the multiple channels for defects detected on other wafers and the actual sizes of the defects detected on the other wafers. The actual sizes of the defects on the other wafers may be determined as described herein. In an additional embodiment, the subgroups are defined such that different subgroups correspond to different size ranges of the defects. For example, defect size is related to scattering intensity. Therefore, the scattering intensity can be used to separate defects into subgroups based on the sizes of the defects. In a further embodiment, the subgroups are defined such that different subgroups correspond to different size ranges of the defects, different heights of the defects, and different layers on which the defects were detected. For example, as shown in step 28 of FIG. 1, defects may be grouped (e.g., as small, medium, large, and special cases) based on the scattering properties (outlines).

In this manner, after the first grouping step described above (or the pre-grouping), each category can be fine-grouped as small, large, and special cases. Defects are grouped by one detected channel intensity and NAP. If the NAP for the defects is smaller than a small NAP cutline, the defects are grouped into a "small" defect category. If the NAP for the defects is greater than the small NAP cutline, the defects are grouped into a large defect category.

The method also includes determining the sizes of the defects in one or more of the subgroups separately based on the output acquired for the defects by only one of the multiple channels and a calibration parameter. The calibration parameter is different for each of the subgroups. In this manner, the defects in different subgroups have different calibration parameters. In addition, the calibration parameter is acquired by using another system to measure actual sizes of defects detected on other wafers. For example, the calibration parameters may be determined using the reference size of a population of sampled defects from a measure of the "ground-truth" defect size such as SEM analysis. However, the "ground-truth" defect size may be determined using any other suitable metrology analysis known in the art. The "ground-truth" defect size determined for the defects detected on other wafers may then be correlated to the output of the multiple channel that will be used to determine the defect size. In this manner, the "ground-truth" data may be used to essentially calibrate the output of the multiple channel used to determine defect size to the actual size of the defects. The analysis performed to measure the actual sizes of the defects detected on other wafers may also include determining any other information about the detects.

In some embodiments, the only one of the multiple channels includes a normalized channel. In this manner, in some embodiments, the defect size can be reported as a function of scattering intensity and defective area from one normalized channel using a calibration parameter. Although different calibration parameters are used to determine the sizes of defects in different subgroups, the sizes of the defects in the different subgroups may be determined using the output acquired by the same multiple channel. In other words, output generated by the same normalized channel may be used to determine the sizes of defects in different subgroups. In addition, as shown in FIG. 1, the method may include calculating size based on scattering properties and scale factors in step 40. Results 42 of the method shown in FIG. 1 may, therefore, include the determined sizes.

In one embodiment, the output acquired by the only one of the multiple channels used to determine the sizes of the one or more of the defects includes scattering intensity and area of the defects. For example, after the grouping steps described above, defect size may be determined based on intensity and NAP. In another embodiment, the output acquired by the only one of the multiple channels used to determine the sizes of the one or more of the defects includes total scattering energy from the defects. In particular, we have found that total scattering energy from the defects correlated best with defect size after grouping similar types of defects into one group. Total scattering energy from the defects may be determined in any suitable manner. As described above, therefore, the embodiments may utilize multi-channel intensity and area information to group defects and then size the defects using single channel intensity and area information with ground-truth data from a SEM or any other suitable source.

In one embodiment, the determining step includes determining the sizes of the one or more of the defects in the one or more of the subgroups separately using different types of functions for at least two of the subgroups. In one such embodiment, the different types of functions are based on the output acquired for the defects by the only one of the multiple channels and the calibration parameters. For example, FIG. 2 (taken from "Wafer inspection Technology Challenges for ULSI Manufacturing," Stokowski et al., which is incorporated by reference as if fully set forth herein) shows scattering measurements (scattered intensity) for polystyrene latex (PSL) spheres on silicon with 70 degree incident angles, s polarization and p polarization, and normal polarization incidence. The collector used to collect the scattered light covers polar angles from about 25 degrees to about 70 degrees and nearly 360 degrees in azimuth.

Figure 2:
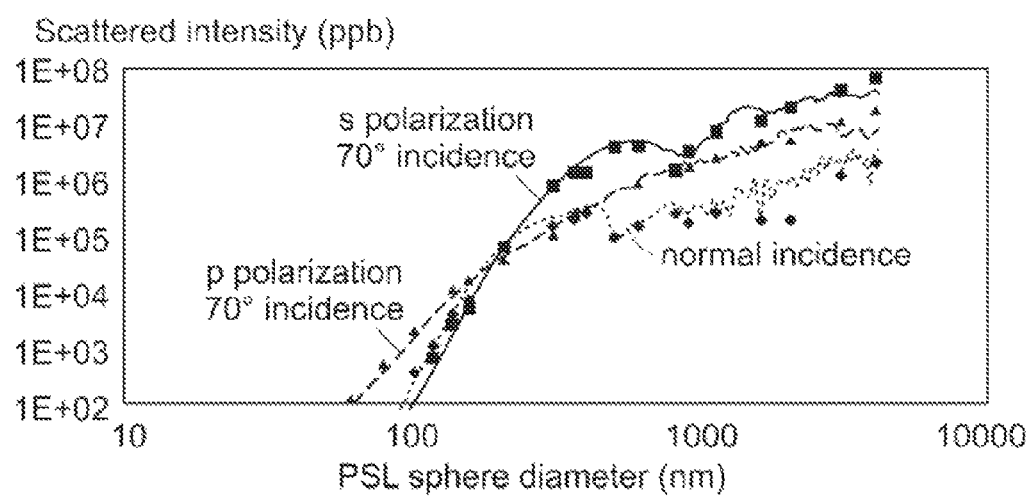
FIG. 2 is a plot illustrating scattering measurements for different sizes of polystyrene latex (PSL) spheres on silicon with 70 degree incident angle, s polarization and p polarization, and normal polarization incidence.

Based on the scattering intensity versus PSL sphere diameter results shown in FIG. 2, small particle diameter is a linear function of scattering intensity, and large particle diameter is a nonlinear function of scattering intensity. Therefore, the sizes of small defects and large defects may be determined using different sizing functions e.g., linear and nonlinear functions, respectively). The relationship between the size, area, and intensity is also based on the physics and architecture of a given optical system. For example, for one system, defect size may be determined using equations (1) and (2) based on the different behavior of large defects and small defects.

Small defects may be defined as those defects whose size cannot be resolved by the point spread function (PSF) of the inspection system, which is usually the same size as the spot size of the inspection system. For example, the spot size of some inspection systems may be 9 pixels. Therefore, the small NAP cutline may be 9 pixels, in this example, the sizes of defects smaller than 9 pixels may be determined using equation 1. Otherwise, equation 2 may be used to determine defect size.

Small Defect:

$$\text{Size} = \text{calibration\_parameter1} * F1(\text{intensity}, \text{NAP}) \qquad (1)$$

Large Defect:

$$\text{Size} = \text{calibration\_parameter2} * F2(\text{intensity}, \text{NAP}) \qquad (2)$$

In another embodiment, the determining step includes determining the sizes of the one or more of the defects in the one or more of the subgroups separately using the same type of function for at least two of the subgroups. In one such embodiment, the same type of function for each of the at least two of the subgroups is based on the calibration parameter that is different for each of the subgroups. For example, defects in different subgroups have different calibration parameters. The sizes of defects separated into special cases type subgroups may be determined using separate calibration parameters but with the same equations. The calibration parameters are based on the reference size of sampled defects such as a defect size determined by SEM analysis.

In one embodiment, the defects are detected on different layers on the wafer. Defects may be detected on different layers on the wafer in different inspection processes performed after the different layers are formed on the wafer. The different inspection processes may be performed as described herein. In addition, the inspection processes performed after different layers are formed on the wafer may be performed using the same parameters for the inspection processes (e.g., the same inspection process) or using one or more different parameters for the inspection processes (e.g., different inspection processes). The inspection processes that are performed on different layers may be selected based on one or more characteristics of the layers, defects of interest for the different layers, etc.

In one such embodiment, the sizes determined for the defects detected on the different layers that are separated into the same subgroup are determined using different calibration parameters. For example, the sizes for defects that are separated into a large subgroup on one layer may be determined using a calibration parameter that is different than that used for determining sizes of defects in a large subgroup on a different layer. In this manner, the calibration parameters for one or more (or each) of the subgroups detected on one or more (or each) of the different layers formed on a wafer may be tuned for the different layers. As such, the calibration parameters used to determine the sizes of defects detected on one or more (or each) of the different layers may be optimized for the different layers, thereby optimizing the performance of the method for each of the different layers.

In another such embodiment, the sizes determined for the defects detected on the different layers that are separated into the same subgroup are determined using the same calibration parameter. For example, the sizes for defects that are separated into a large subgroup on one layer may be determined using the same calibration parameter for determining sizes of defects in a large subgroup on a different layer. The two or more layers for which the same calibration parameter is used for the same subgroup of defects may be similar layers (e.g., similar deposition layers formed in similar deposition processes). The calibration parameters for similar layers may be stored in a library. As such, the performance of the method using such calibration parameters may be referred to as "library performance." Such a library approach is advantageous for ease of use.

In another embodiment, the method includes determining a distribution of the sizes of at least some of the defects detected on the wafer and monitoring a process performed on the wafer based on the distribution. The distribution of the sizes of at least some of the defects detected on the wafer can be determined in any suitable manner. In addition, since the sizes of the defects can be determined substantially accurately using the embodiments described herein, the distribution of the sizes of the defects detected on the wafer can be determined substantially accurately. Since the distribution of the sizes of the defects on the wafer may relatively accurately reflect the performance of the process performed on the wafer (since the distribution may be particularly sensitive to changes in one or more parameters of the process), the relatively accurate distribution can be used to monitor the process relatively accurately. In this manner, any drifts or other changes in the performance of the process can be detected relatively accurately using such monitoring thereby enabling early detection of process problems, which can improve process control and increase yield of the process.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method determines the sizes of the defects, the method may include displaying the defect sizes to a user. Furthermore, the results may be stored "permanently," "semi-permanently," temporarily, or for some period of time. For example, the storage medium may be random access memory (RAM), and the results may not necessarily persist indefinitely in the storage medium.

The embodiments described herein have a number of advantages over other methods and systems for determining sizes of defects detected on wafers. For example, the embodiments described herein improve the accuracy of reported defect sizes on a wafer with dark field scanning inspection systems. Therefore, the embodiments described herein can be used to enhance defect sizing performance of dark field inspection systems. In addition, defect size is substantially important for monitoring semiconductor processes. However, previously used methods such as those that include using intensity to map the defect size are not accurate for different types of defects such as concave and flat particle type defects. The embodiments described herein, however, can be used for determining sizes of such types of defects as well as other different types of defects (e.g., all different types of defects). Furthermore, with more accurate defect size reporting, defect size distribution of wafers can be monitored to control semiconductor processes.

Figure 3:
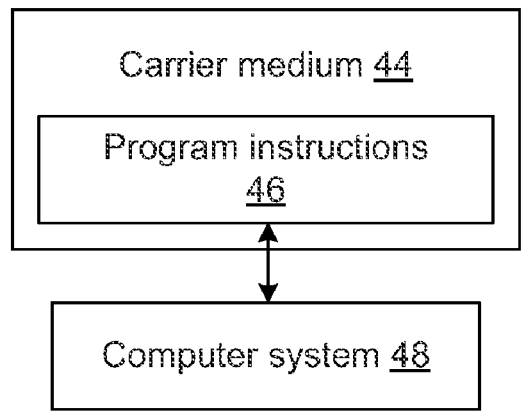
FIG. 3 is a block diagram illustrating one embodiment of a carrier medium that includes program instructions executable on a computer system for performing one or more of the computer-implemented methods described herein.

An additional embodiment relates to a carrier medium that includes program instructions executable on a computer system for performing a computer-implemented method for determining sizes of defects detected on a wafer. One such embodiment is shown in FIG. 3. In particular, as shown in FIG. 3, carrier medium 44 includes program instructions 46 executable on computer system 48.

The computer-implemented method includes separating the defects into groups based on output acquired for the defects by multiple channels of an inspection system used to detect the defects on the wafer. Separating the defects into groups may be performed as described herein. The method also includes separating the defects in one or more of the groups into subgroups based on the output acquired for the defects by one or more of the multiple channels. Separating the defects into subgroups may be performed as described herein. In addition, the method includes determining the sizes of one or more of the defects in one or more of the subgroups separately based on the output acquired for the defects by only one of the multiple channels and a calibration parameter. The calibration parameter is different for each of the subgroups. In addition, the calibration parameter is acquired by using another system to measure actual sizes of defects detected on other wafers. Determining the sizes of the defect (s) may be performed as described further herein. The computer-implemented method for which the program instructions are executable may include any other step(s) described herein.

Program instructions 46 implementing methods such as those described herein may be transmitted over or stored on carrier medium 44. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 4:
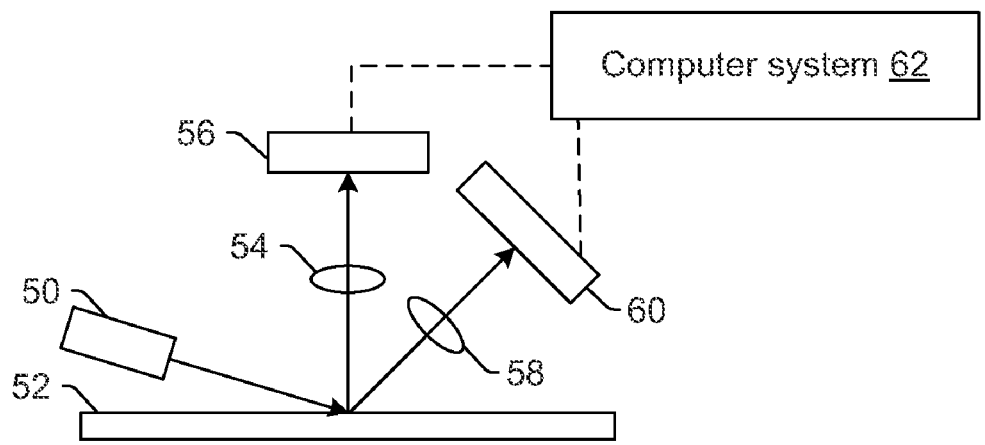
FIG. 4 is a schematic diagram illustrating a system configured to determine sizes of defects detected on a wafer.

Another embodiment relates to a system configured to determine sizes of defects detected on a wafer. One embodiment of such a system is shown in FIG. 4. The system includes an inspection system configured to detect the defects on the wafer and to acquire output for the defects. For example, as shown in FIG. 4, the inspection system includes light source 50. Light source 50 may include any suitable light source known in the art such as a laser. Light source 50 is configured to direct light to wafer 52 at an oblique angle of incidence, which may include any suitable oblique angle of incidence. The inspection system may also include one or more optical components (not shown) that are configured to direct light from light source 50 to wafer 52. The optical components may include any suitable optical components known in the art such as, but not limited to, a polarizing component. In addition, the light source and/or the one or more optical components may be configured to direct the light to the wafer at one or more angles of incidence (e.g., an oblique angle of incidence and/or a substantially normal angle of incidence).

Light scattered from wafer 52 may be collected and detected by multiple channels of the inspection system. For example, light scattered from wafer 52 at angles relatively close to normal may be collected by lens 54. Lens 54 may include a refractive optical element as shown in FIG. 4. In addition, lens 54 may include one or more refractive optical elements and/or one or more reflective optical elements. Light collected by lens 54 may be directed to detector 56. Detector 56 may include any suitable detector known in the art such as a charge coupled device (CCD) or another type of imaging detector. Detector 56 is configured to generate output that is responsive to the light scattered from the wafer. Therefore, lens 54 and detector 56 form one channel of the inspection system. This channel of the inspection system may include any other suitable optical components (not shown) known in the art such as a polarizing component and/or a Fourier filtering component. The inspection system is configured to detect the defects on the wafer and to acquire the output for the defects using the output generated by detector 56. For example, a processor (not shown) of the inspection system may be configured to detect defects on the wafer using the output generated by the detector and to acquire the output generated by the detector corresponding to the defects.

Light scattered from wafer 52 at different angles may be collected by lens 58. Lens 58 may be configured as described above. Light collected by lens 58 may be directed to detector 60, which may be configured as described above. Detector 60 is also configured to generate output that is responsive to the light scattered from the wafer. Therefore, lens 58 and detector 60 may form another channel of the inspection system. This channel may also include any other optical components described above. In some embodiments, lens 58 may be configured to collect light scattered from the wafer at polar angles from about 20 degrees to about 70 degrees. In addition, lens 58 may be configured as a reflective optical element (not shown) that is configured to collect light scattered from the wafer at azimuthal angles of about 360 degrees. The inspection system is configured to detect the defects on the wafer and to acquire the output for the defects using the output generated by detector 60, which may be performed as described above.

The inspection system shown in FIG. 4 may also include one or more other channels. For example, the inspection system may include an additional channel (not shown), which may include any of the optical components described herein, configured as a side channel. In one such example, the side channel may be configured to collect and detect light that is scattered out of the plane of incidence (e.g., the side channel may include a lens that is centered in a plane that is substantially perpendicular to the plane of incidence and a detector configured to detect light collected by the lens). The inspection system may be configured to detect the defects on the wafer and to acquire the output for the defects using the output generated by a detector of the side channel, which may be performed by the inspection system as described above.

The system also includes computer system 62. Output generated by the detectors may be provided to computer system 62. For example, the computer system may be coupled to each of the detectors (e.g., by one or more transmission media shown by the dotted lines in FIG. 4, which may include any suitable transmission media known in the art) such that the computer system may receive the output generated by the detectors. The computer system may be coupled to each of the detectors in any suitable manner.

The computer system is configured to separate the defects into groups based on the output acquired for the defects by multiple channels of the inspection system. The output acquired by the multiple channels used to separate the defects into the groups may include output acquired by any two or more channels of the inspection system. The output that is used to separate the defects into the groups may vary depending on, for example, the types of defects that are detected on the wafer (e.g., since different types of defects scatter light into different channels differently as described further herein). The computer system may be configured to separate the defects into groups as described further herein.

The computer system is also configured to separate the defects in one or more of the groups into subgroups based on the output acquired for the defects by one or more of the multiple channels. The output acquired by the one or more multiple channels used to separate the defects into subgroups may include output acquired by any one or more channels of the inspection system. The computer system may be configured to separate the defects into the subgroups as described further herein.

The computer system is further configured to determine the sizes of one or more of the defects in one or more of the subgroups separately based on the output acquired for the defects by only one of the multiple channels and a calibration parameter. The calibration parameter is different for each of the subgroups. In addition, the calibration parameter is acquired by using another system to measure actual sizes of defects detected on other wafers. The computer system may be configured to determine the sizes of the defects according to any of the embodiments described herein.

The computer system may be configured to perform any other step(s) of any method embodiment(s) described herein. The computer system may be further configured as described herein. The inspection system may also be further configured as described herein. Furthermore, the system may be further configured as described herein.

It is noted that FIG. 4 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the Puma 9000 and 9100 series of tools that are commercially available from KLA-Tencor; San Jose, Calif. For some such systems, the methods described herein may be provided as optional functionality of the system (e.g., in addition to other functionality of the system). Alternatively, the system described herein may be designed "from scratch" to provide a completely new system.

In some embodiments, a system configured to perform one or more of the computer-implemented methods described herein may include an inspection system such as that described above. However, a system that is configured to perform one or more of the computer-implemented methods described herein may not include an inspection system. For example, the system may include one or more processors or one or more computer systems configured as a stand alone tool. In one such example, the system may include one or more components that are specifically designed (and optionally dedicated) to performing one or more of the computer-implemented methods described herein.

Further modifications and alternative embodiments of various aspects of the invention may be apparent to those skilled in the art in view of this description. For example, computer-implemented methods, carrier media, and systems for determining sizes of defects detected on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for determining sizes of defects detected on a wafer, comprising:
    separating the defects into groups based on output acquired for the defects by multiple channels of an inspection system used to detect the defects on the wafer, wherein a first lens and a first detector form a first of the multiple channels, wherein a second lens and a second detector form a second of the multiple channels, and wherein the first and second lenses collect light scattered from the wafer at different angles;
    separating the defects in one or more of the groups into subgroups based on the output acquired for the defects by one or more of the multiple channels; and
    determining the sizes of one or more of the defects in one or more of the subgroups separately based on the output acquired for the defects by only one of the multiple channels and a calibration parameter, wherein the calibration parameter is different for each of the subgroups, wherein the calibration parameter is acquired by using another system to measure actual sizes of defects detected on other wafers, and wherein said separating the defects into the groups, said separating the defects into the subgroups, and said determining are performed using a computer system.

2. The method of claim 1, wherein the inspection system comprises a dark field inspection system.

3. The method of claim 1, further comprising determining a distribution of the sizes of at least some of the defects detected on the wafer and monitoring a process performed on the wafer based on the distribution.

4. The method of claim 1, wherein the output acquired by the multiple channels used to separate the defects into the groups comprises scattering intensity.

5. The method of claim 1, wherein the groups are defined based on how different types of defects scatter light into the multiple channels.

6. The method of claim 1, wherein the groups are defined such that different groups correspond to different types of defects.

7. The method of claim 1, wherein the output acquired by the one or more of the multiple channels used to separate the defects into the subgroups comprises one or more properties of images of the defects.

8. The method of claim 1, wherein the output acquired by the one or more of the multiple channels used to separate the defects into the subgroups comprises one or more properties of images of the defects, and wherein the one or more properties comprise a scattering intensity, an area, a gradient, or some combination thereof.

9. The method of claim 1, wherein the subgroups are defined based on a correlation between the output acquired by the one or more of the multiple channels for the defects detected on the other wafers and the actual sizes of the defects detected on the other wafers.

10. The method of claim 1, wherein the subgroups are defined such that different subgroups correspond to different size ranges of the defects.

11. The method of claim 1, wherein the subgroups are defined such that different subgroups correspond to different size ranges of the defects, different heights of the defects, and different layers on which the defects were detected.

12. The method of claim 1, wherein separating the defects into the subgroups comprises determining scattering intensity and area of the defects using the output acquired by the one or more of the multiple channels.

13. The method of claim 1, wherein the output acquired by the only one of the multiple channels used to determine the sizes of the one or more of the defects comprises scattering intensity and area of the defects.

14. The method of claim 1, wherein the output acquired by the only one of the multiple channels used to determine the sizes of the one or more of the defects comprises total scattering energy from the defects.

15. The method of claim 1, wherein the only one of the multiple channels comprises a normalized channel.

16. The method of claim 1, wherein said determining comprises determining the sizes of the one or more of the defects in the one or more of the subgroups separately using different types of functions for at least two of the subgroups, and wherein the different types of functions are based on the output acquired for the defects by the only one of the multiple channels and the calibration parameters.

17. The method of claim 1, wherein said determining comprises determining the sizes of the one or more of the defects in the one or more of the subgroups separately using the same type of function for at least two of the subgroups, and wherein the same type of function for each of the at least two of the subgroups is based on the calibration parameter that is different for each of the subgroups.

18. The method of claim 1, wherein the defects are detected on different layers on the wafer, and wherein the sizes determined for the defects detected on the different layers that are separated into the same subgroup are determined using different calibration parameters.

19. The method of claim 1, wherein the defects are detected on different layers on the wafer, and wherein the sizes determined for the defects detected on the different layers that are separated into the same subgroup are determined using the same calibration parameter.

20. The method of claim 1, wherein the first and second detectors are not different portions of the same detector.

21. A non-transitory computer readable medium containing computer instructions stored therein for causing a computer processor to perform a computer-implemented method for determining sizes of defects detected on a wafer, wherein the computer-implemented method comprises:

separating the defects into groups based on output acquired for the defects by multiple channels of an inspection system used to detect the defects on the wafer, wherein a first lens and a first detector form a first of the multiple channels, wherein a second lens and a second detector form a second of the multiple channels, and wherein the first and second lenses collect light scattered from the wafer at different angles;

separating the defects in one or more of the groups into subgroups based on the output acquired for the defects by one or more of the multiple channels; and determining the sizes of one or more of the defects in one or more of the subgroups separately based on the output acquired for the defects by only one of the multiple channels and a calibration parameter, wherein the calibration parameter is different for each of the subgroups, and wherein the calibration parameter is acquired by using another system to measure actual sizes of defects detected on other wafers.

22. A system configured to determine sizes of defects detected on a wafer, comprising:

an inspection system configured to detect the defects on the wafer and to acquire output for the defects; and a computer system configured to:

separate the defects into groups based on the output acquired for the defects by multiple channels of the inspection system, wherein a first lens and a first detector form a first of the multiple channels, wherein a second lens and a second detector form a second of the multiple channels, and wherein the first and second lenses collect light scattered from the wafer at different angles;

separate the defects in one or more of the groups into subgroups based on the output acquired for the defects by one or more of the multiple channels; and determine the sizes of one or more of the defects in one or more of the subgroups separately based on the output acquired for the defects by only one of the multiple channels and a calibration parameter, wherein the calibration parameter is different for each of the subgroups, and wherein the calibration parameter is acquired by using another system to measure actual sizes of defects detected on other wafers.

* * * * *